(12) United States Patent
Hartstein et al.

(10) Patent No.: US 10,106,767 B2
(45) Date of Patent: Oct. 23, 2018

(54) TRANSFER DEVICE

(71) Applicant: Airbus DS GmbH, Taufkirchen (DE)

(72) Inventors: Heinz Hartstein, Tettnang (DE); Peter Kern, Salem (DE)

(73) Assignee: Airbus DS GmbH, Taufkirchen (DE)

( * ) Notice: Subject to any disclaimer, the term of this patent is extended or adjusted under 35 U.S.C. 154(b) by 0 days.

(21) Appl. No.: 15/452,807

(22) Filed: Mar. 8, 2017

(65) Prior Publication Data

US 2017/0260491 A1  Sep. 14, 2017

(30) Foreign Application Priority Data

Mar. 10, 2016 (DE) .................. 161 59 673

(51) Int. Cl.
| | |
|---|---|
| *C12M 1/00* | (2006.01) |
| *C12M 1/36* | (2006.01) |
| *C12Q 3/00* | (2006.01) |
| *C12M 1/34* | (2006.01) |

(52) U.S. Cl.
CPC ............ *C12M 29/00* (2013.01); *C12M 21/02* (2013.01); *C12M 29/22* (2013.01); *C12M 41/34* (2013.01); *C12M 41/40* (2013.01); *C12M 41/48* (2013.01); *C12Q 3/00* (2013.01)

(58) Field of Classification Search
CPC ...... C12M 21/00; C12M 21/02; C12M 23/06; C12M 23/22; C12M 31/10; C12M 31/02; C12M 31/08; C12M 31/12; C12M 31/00; C12M 29/00; C12M 29/22; C12M 41/40; C12M 41/34; C12M 41/48; C12M 43/06; C12M 43/08; C12N 1/12; C12N 1/10; C12N 1/20; C12N 13/00; C12P 5/023; C12P 7/649; C12Q 3/00; C01F 3/32; Y02E 50/13; Y02E 50/343

USPC .................. 47/1.4; 435/292.1, 290.1–290.4

See application file for complete search history.

(56) References Cited

U.S. PATENT DOCUMENTS

| | | |
|---|---|---|
| 3,224,143 A | 12/1965 | Tew et al. |
| 4,868,123 A | 9/1989 | Berson et al. |
| 5,028,309 A | 7/1991 | Nishizawa et al. |
| 5,122,255 A | 6/1992 | Noda et al. |
| 6,177,001 B1 * | 1/2001 | Meyer ............... G01N 27/4175 204/427 |
| 2007/0000780 A1 * | 1/2007 | Oya ..................... G01N 27/419 204/424 |
| 2008/0220514 A1 | 9/2008 | Lu |

(Continued)

FOREIGN PATENT DOCUMENTS

| | | |
|---|---|---|
| EP | 0 047 434 A1 | 3/1982 |
| JP | S53-146798 A | 4/1977 |

(Continued)

OTHER PUBLICATIONS

Office Action dated Apr. 18, 2017 issued in corresponding JP application No. 2017-033273 (and English translation).

(Continued)

*Primary Examiner* — Michael L Hobbs (74) *Attorney, Agent, or Firm* — Posz Law Group, PLC (57) ABSTRACT

A transfer device includes at least one pump unit provided for a defined gas transfer between a first, closed-off space of an installation, in particular a photobioreactor installation, and a second space which is separate from the first space. The at least one pump unit is embodied as a selective oxygen pump.

18 Claims, 2 Drawing Sheets

(56) References Cited

U.S. PATENT DOCUMENTS

2012/0088296 A1* 4/2012 Vargas .................. C12M 21/02
                                                                    435/292.1
2016/0289621 A1* 10/2016 Oelschlager ........... C12M 23/14

FOREIGN PATENT DOCUMENTS

| JP | S60-126075 A | 7/1985 |
| JP | H01-213568 A | 8/1989 |
| JP | H01-291783 A | 11/1989 |
| JP | H02-141526 A | 5/1990 |
| JP | H04-161223 A | 6/1992 |
| JP | H05-502158 A | 4/1993 |
| JP | H08-337404 A | 12/1996 |
| WO | 91/08314 A1 | 6/1991 |

OTHER PUBLICATIONS

Extended European Search Report dated Aug. 30, 2016 issued in corresponding EP patent application No. 16159673.9 (and partial English translation).
Office Action dated Nov. 28, 2017 issued in corresponding JP application No. 2017-033273 (and English translation).
NGK Insulators, Ltd., "Bringing the world's first high-precision NOx sensor to market" NGK News, Jun. 11, 2008.

* cited by examiner

TRANSFER DEVICE

CROSS REFERENCE TO RELATED APPLICATION

This application is based on and incorporates herein by reference European Patent Application No. 16159673.9 filed on Mar. 10, 2016.

STATE OF THE ART

The invention relates to a transfer device.

A transfer device with at least one pump unit, which is provided for a defined gas transfer between a first, closed-off space of an installation and a second space, which is separate from the first space, has already been proposed. This kind of transfer device is, for example, used for pumping gas out of the first, closed-off space of a photobioreactor as continuous operation of the bioreactor, with $CO_2$ being added continuously or portion-wise, results in a pressure increase in the first space. Herein a portion of the entire gas mix is pumped off, as a result of which usually oxygen $O_2$, carbon dioxide $CO_2$ and nitrogen $N_2$ are pumped out of the space.

The objective of the invention is in particular to make a generic device available which has improved characteristics regarding control of a gas transfer, in particular a selective gas transfer, as well as regarding control of gas ratios. The objective is achieved, according to the invention, by the features of patent claim 1, while advantageous implementations and further developments of the invention may be gathered from the subclaims.

ADVANTAGES OF THE INVENTION

The invention is based on a transfer device with at least one pump unit provided for a defined gas transfer between a first, closed-off space of an installation, in particular a photobioreactor installation, and a second space, which is separate from the first space.

It is proposed that the at least one pump unit is embodied as a selective oxygen pump. Preferably the pump unit is implemented by an electro-chemical oxygen pump. Preferentially the transfer device is implemented by a photobioreactor transfer device. By a "transfer device" is in particular, in this context, a device of an installation to be understood which is provided for defined feeding in or conveying away a fluid, in particular a gas, for an installation. Preferably it is in particular to be understood as a device provided for a defined gas transfer out of at least one closed-off space of the installation. Via the transfer device, for example, a pressure compensation and/or a transition, in particular a selective transition, of gases between at least two spaces which are separate from each other is achievable. By a "photobioreactor transfer device" in particular, in this context, a transfer device of a photobioreactor is to be understood, which is provided for defined feeding in or conveying away a fluid, in particular a gas, for the photobioreactor. Furthermore, in this context, a "pump unit" is in particular to be understood as a unit provided for conveying at least one fluid. Preferably it is in particular to be understood as a unit provided for a direct, defined gas transfer between at least two spaces which are separate from each other. A gas transfer is herein in particular achievable independently from a pressure difference between the two spaces which are separate from each other. Moreover, by a "closed-off space" is in particular, in this context, a space to be understood which is in at least one operating state, preferably during operation of the installation, at least substantially screened off and/or closed off from an environment regarding a free air flow and the environment. Preferentially it is in particular to be understood as a space in which unintended matter transition from the space and/or into the space is prevented or at least restricted. Preferably the space is hermetically closed against an environment and/or against at least one adjacent space. By an "installation" is in particular, in this context, a device to be understood comprising at least one reactor and/or at least one process. Preferentially it is to be understood as a device comprising at least one reactor for physio-chemical, biochemical and/or biological processes. Especially preferably it is in particular to be understood as a device comprising at least one reactor, which releases oxygen in processes. By a "photobioreactor installation" is in particular, in this context, a reactor or an installation to be understood which is provided for production and/or cultivation of microorganisms, e.g. algae, cyanobacteria, moss plants, bacteria, phytocell cultures and/or other microorganisms, in particular within an artificial technical environment. Preferably it is in particular to be understood as a reactor or installation utilizing the photosynthesis process of produced and/or cultivated microorganisms to obtain energy, in particular for binding carbon dioxide $(CO_2)$ by means of light and for generating oxygen $(O_2)$ via photosynthesis. Furthermore, in this context, a "selective oxygen pump" is in particular to be understood as a pump unit which is in particular selective for oxygen. Preferentially it is in particular to be understood as a pump unit by means of which oxygen may be pumped selectively. Preferably it is in particular to be understood as a pump unit by means of which, independently from a prevailing gas mixture, oxygen—if present—may be selectively pumped out of a space and/or transferred into another space. "Provided" is in particular to mean specifically programmed, designed and/or equipped. By an object being provided for a certain function is in particular to be understood that the object fulfills and/or implements said certain function in at least one application state and/or operating state.

By the implementation of the transfer device according to the invention, oxygen may advantageously be transferred, depending on requirement, specifically and selectively. This allows in particular achieving purposeful controlling, reducing and/or increasing an oxygen concentration, in particular in the first, closed-off space of the installation, in particular the photobioreactor installation. In this way advantageously control of a gas transfer as well as a simultaneous control of a gas ratio and/or of the overall pressure is achievable. Preferably this allows providing a transfer device, which in particular works completely electrically.

It is also proposed that the at least one pump unit comprises at least one zirconium oxide element, which is provided for a selective transfer of oxygen out of the first space into the second space. Preferentially the zirconium oxide element is implemented by a zirconium oxide ceramic. Preferably the zirconium oxide element is provided to act as an ion conductor and/or as a solid-matter electrolyte. Particularly preferably furthermore a pump rate of the pump unit is in particular influenced by a current rating applied and/or a geometry, in particular a surface area, of the zirconium oxide element. Preferentially the pump performance, i.e. a volume flow per time unit, and the achievable pressures, in particular both on a suction side and on an output side, may be adjusted and/or configured via a pump flow, an operating temperature and by the geometrical dimensions of the pump unit. By means of the transfer device further the oxygen production rate of the process, in particular the photosynthesis rate of oxygen ($O_2$), or the oxygen transfer rate may be determined. Preferably the zirconium oxide element is provided for selective transfer of oxygen from the first space into the second space under ambient pressure. A "zirconium oxide ceramic" is in particular to mean, in this context, a technical ceramic. Preferably the zirconium oxide ceramic is embodied of a non-metal mineral material. The zirconium oxide ceramic is in particular stabilized with other oxides, e.g. calcium oxide (CaO), magnesia oxide (MgO) and/or yttrium oxide ($Y_2O_3$). Principally, however, other ceramics and/or elements deemed expedient by someone skilled in the art are also conceivable, e.g. a ceramic and/or an element comprising titanium oxide, vanadium oxide, niobium oxide and/or perovskite, wherein the oxides may respectively be stabilized by other oxides. An operating pressure of the first space may be between $10^{-3}$ mbar and 100 bar. An operating pressure of the second space may also be between $10^{-3}$ mbar and 100 bar. This in particular allows making a particularly reliable pump unit available. Furthermore in this way an advantageously flexible pump rate of the pump unit may be rendered possible. In addition, by an appropriate configuration no periodic exchange of consumable material is necessary for operation. No operator time is required therefor. Low demand of resources is thus also achievable. A transfer device of high operational robustness, and hence of preference for use in outer space, may be rendered available. In particular, a pump unit free of mobile parts may be rendered available. Preferably a transfer device may be rendered available, which in particular works completely electrically.

It is further proposed that the at least one pump unit comprises at least one heating element, which is provided for heating the at least one zirconium oxide element. Preferably the at least one heating element is provided for heating the zirconium oxide element to an operating temperature and in particular keep it at this temperature. Preferentially the at least one heating element is provided for heating the zirconium oxide element up to an operating temperature of at least 500° C., particularly preferably an operating temperature of 500° to 700° C., and in particular keep it at this temperature. By a "heating element" is in particular, in this context, an element to be understood which is provided for generating a heating output. It is preferably in particular to be understood as an element which is provided for converting energy, in particular electrical energy, into heat energy. Various implementations of a heating element are conceivable which are deemed expedient by someone skilled in the art. The heating element may, for example, be embodied as a microwave heating element, as a resistance heating element and/or particularly preferably as an infrared heating element. This allows advantageously providing the zirconium oxide element with an optimum operating temperature. It further allows an optimum oxygen transfer. In particular, a high efficiency level of the pump unit is achievable in this way.

It is also proposed that the at least one zirconium oxide element of the at least one pump unit is implemented by a doped zirconium oxide element. Preferably the zirconium oxide element is doped, for example, with yttrium oxide ($Y_2O_3$). Principally, it would however also be conceivable that the zirconium oxide element is implemented by a non-doped zirconium oxide element and/or by a combination of doped and non-doped zirconium oxide elements. In this way an advantageously effective pump unit may be rendered available. Furthermore, in particular an advantageously high ionic conductivity of the zirconium oxide element is achievable.

It is further proposed that the at least one zirconium oxide element of the at least one pump unit is provided, depending on a polarity of a pump flow, for a bi-directional oxygen transfer between the first space and the second space. Preferentially this is in particular to mean that oxygen is conveyable from the first space into the second space as well as from the second space into the first space by means of the pump unit. Preferably choosing a direction of an oxygen transition is effected in particular via changing a polarity of a potential applied. This allows in particular achieving an advantageously variable use of the pump unit. Furthermore the pump unit may in this way be advantageously used for a bi-directional oxygen transfer between the first space and the second space, in particular in case of equivalent physical set-up.

The at least one pump unit is further provided for specifically and selectively separating off oxygen. This in particular allows specific and selective transfer of oxygen. In particular, control of gas transfer and simultaneous control of a partial pressure and/or of the overall pressure are advantageously achievable.

It is moreover proposed that the at least one pump unit is in at least one operating state provided for an electrical reduction of at least one gas. Preferably the at least one pump unit is in at least one operating state provided for an electrical reduction of at least one gas in the first space. In this way an advantageously efficient pump unit may be made available.

Further it is proposed that the at least one pump unit is provided for an accumulation of a reduced gas in the first space and/or the second space. Preferably the at least one pump unit is provided for an accumulation of a reduced gas in the first space. In this way in particular specific and selective gas accumulation may be rendered possible.

It is also proposed that the transfer device comprises at least one measuring unit, which is provided for capturing a voltage difference between at least two sides of the pump unit. Preferentially the measuring unit is provided for capturing a voltage difference between a first side of the pump unit, which is arranged in the first space, and a second side of the pump unit, which is arranged in the second space. Preferably the measuring unit comprises at least one voltmeter which is provided for capturing a voltage difference between at least two contact points, in particular between at least two electrodes. Especially preferentially the measuring unit moreover comprises a computing unit, which is provided for an evaluation of measuring signals of the voltmeter. By a "computing unit" is in particular a unit to be understood with an information input, an information processing and an information output. Advantageously the computing unit comprises at least a processor, a memory, input and output elements, further electrical structural components, an operating program, ratio control routines, control routines and/or calculating routines. Principally, however, the computing unit may also be embodied as a logic switch, e.g. as an FPGA (Field Programmable Gate Array), and/or as an analogous switch. Due to this, the pump unit may be used in particular additionally for capturing data. Preferably this allows the pump unit taking on an additional monitoring function.

It is also proposed that the at least one measuring unit is provided for deducting a pressure difference between the first space and the second space on the basis of the voltage difference. The at least one measuring unit is provided to deduct a partial-pressure difference between the first space and the second space depending on the voltage difference. Particularly preferably a present oxygen concentration and/or differences of the oxygen concentration may be determined, in particular if an oxygen partial pressure in the first space and/or in the second space is known. In this way the transfer device may be advantageously used for pressure monitoring.

The invention is furthermore based on an installation, in particular a photobioreactor installation, with a transfer device. It is proposed that the installation comprises a control and/or regulation unit, which is provided for controlling and/or regulating an absolute oxygen partial fraction in the first space outside a reaction area by means of the transfer device. Preferentially the control and/or regulation unit is provided for controlling and/or regulating an absolute oxygen partial fraction in the first space outside a reaction area to a value of maximally 25%, preferably no more than 20% and particularly preferably of maximally 15%. Principally, however, other values of the oxygen partial fraction deemed expedient by someone skilled in the art are also conceivable, in particular depending on a type of use. Preferentially the control and/or regulation unit is provided for controlling and/or regulating an absolute oxygen partial fraction in the first space outside a reaction area to a value of approximately 15%. Especially preferentially the control and/or regulation unit is provided for controlling an absolute oxygen partial fraction in the first space outside a reaction area to a value in such a way that a ratio of $dCO_2/dt=-dO_2/dt$ is achieved that is equimolar as regards its absolute value. Preferably the control and/or regulation unit is provided for controlling and/or regulating an absolute oxygen partial fraction in the first space outside a reaction area by pumping off oxygen by means of the transfer device. By a "control and/or regulation unit" is in particular a unit to be understood with at least a control electronics component. A "control electronics component" is in particular to mean a unit with a processor unit and with a memory unit as well as with an operating program stored in the memory unit. Principally, however, the control electronics component may also be implemented as a logic switch, e.g. an FPGA (Field Programmable Gate Array), and/or as an analogous switch. In this way an advantageous gas mixture may be provided in the first space of the installation, in particular the photobioreactor installation. Preferably this allows advantageously controlling and/or regulating an absolute oxygen partial fraction in the first space to a value at which there is an advantageous, in particular optimum, $O_2$ production rate and/or $O_2$ output rate of the installation, in particular the photobioreactor installation. In this way in particular a complete integration of the transfer device into an automatic, in particular computer-based control and/or regulation concept may be rendered possible.

It is further proposed that the installation, in particular the photobioreactor installation, comprises at least one photobioreactor unit, which is provided for receiving fed-in carbon dioxide and for generating and outputting oxygen via photosynthesis. Principally, however, it is also conceivable that the installation comprises at least one alternative reactor unit which is provided to generate and output oxygen. By a "photobioreactor unit" is in particular, in this context, a unit to be understood which is provided for direct production and/or cultivation of microorganisms, e.g. algae, cyanobacteria, moss plants and/or phyto-cell cultures, in particular within an artificial technical environment. It is preferably in particular to be understood as a unit directly using the photosynthesis process of produced and/or cultivated microorganisms for generating the oxygen ($O_2$) via photosynthesis with light, carbon dioxide ($CO_2$) and water. For this purpose the unit preferentially comprises a light source for irradiating the microorganisms. This allows making an advantageous installation available.

Furthermore the invention relates to a method for operating the installation, in particular the photobioreactor installation. It is proposed that an absolute oxygen partial fraction in the first space outside a reaction area is controlled and/or regulated via the transfer device. Preferably the absolute oxygen partial fraction in the first space outside a reaction area is controlled and/or regulated via the transfer device to a value of maximally 25%, preferably of no more than 20% and particularly preferably of maximally 15%. Especially preferentially the absolute oxygen partial fraction in the first space outside a reaction area is controlled and/or regulated via the transfer device to a value of approximately 15%. Particularly preferably the absolute oxygen partial fraction in the first space outside a reaction area is controlled and/or regulated via the transfer device to a value in such a way that a ratio of $dCO_2/dt=-dO_2/dt$ is achieved which is equimolar as regards its absolute value. In this way it is possible to make an advantageous gas mixture available in the first space of the installation, in particular the photobioreactor installation. Preferentially in this way an absolute oxygen partial fraction in the first space may be advantageously controlled and/or regulated to a value at which there is an advantageous, in particular optimum $O_2$ production rate of the installation.

It is also proposed that the transfer device is made use of for monitoring and/or adjusting at least one safety-relevant operating state. Preferably the transfer device may be used, for example, for monitoring and/or adjusting a pressure and/or an oxygen concentration in the second space and/or particularly preferably in the first space. This in particular allows achieving an advantageously diverse use of the transfer device. Preferentially the transfer device may in this way advantageously fulfill a function beyond a transfer.

Furthermore it is proposed that the performance is effected under conditions of reduced and/or increased gravity. Preferably said method is to be used in outer space, e.g. at μg in a spaceship, in a process in a spaceship at accelerations from $10^{-6}$ xg to 10 xg, on a planet, e.g. Mars, and/or on a natural satellite, e.g. the moon. The g values are herein in particular to be understood on a planet and/or an asteroid or in a traveling spaceship. Principally, however, a g value may be drastically increased for technical reasons, e.g. to 100 xg. For example, an installation and/or a reactor may be exposed to an artificial process acceleration which differs from the values mentioned. "Conditions of reduced gravity" are in particular to be understood as conditions under which there is a gravitational effect of maximally 0.9 xg, advantageously minimally up to $1*10^{-3}$ xg, preferably of minimally up to $1*10^{-6}$ xg and especially preferentially of minimally up to $1*10^{-8}$ xg. Moreover, "conditions of increased gravity" are in particular to be understood as conditions under which there is a gravitational effect of at least 1.1 xg, preferably up to maximally 10 xg. The gravitational effect may be caused by gravity and/or generated artificially by an acceleration. The g values may principally be increased drastically for technical reasons. "g" designates the value of the gravitational acceleration on Earth, namely 9.81 ml $*s^{-2}$. The method is advantageously applicable in live-sustaining systems and/or in climate control systems in outer space, e.g. in spacecraft, space habitats, greenhouses, manned systems like the rover, and/or space suits, in particular EVA suits (Extra Vehicular Activity suits).

It is further proposed that the method is performed in an ISRU (In-Situ Ressource Utilisation) application. The method may herein be applied for separating off and/or accumulating oxygen from a gas mixture and/or from locally present material, e.g. a locally present solid-matter body, within the range of In-Situ Ressource Utilisation (ISRU) applications on planets. Beyond this the method may be alternatively also applied in closed compartments in terrestric applications, e.g. in airplanes, submarines, bunkers, hermetically closed-off spaces, greenhouses and/or vehicles, like cars, trains, etc. As a result of this, an advantageous application of the method is achievable.

Moreover it is proposed that the method is used as part of an Environmental Control System. The method is herein in particular used for pressure regulation and/or temperature regulation and/or for splitting gases, e.g. carbon dioxide (CO2) to obtain oxygen (o2) and/or for controlled oxygen supply and/or regulation. Preferably the method is used for pressure regulation and temperature regulation as well as for oxygen supply in at least substantially closed systems, e.g. in particular in spacecraft, aircraft, landcraft or watercraft. The method is herein in particular performable in an Environmental Control System on Earth as well as in outer space, in spacecraft and/or on planets and/or asteroids. An "Environmental Control System" is to mean, in this context, in particular a control system for surroundings. Preferentially it is in particular to be understood as a climate system provided for air exchange, pressure regulation, temperature regulation, pressure supply and/or oxygen supply, in particular in an at least substantially closed cabin. Preferably it is in particular to be understood as a climate system of a spacecraft and/or airplane, in particular a commercial airplane. As a result of this, an advantageous application of the method is achievable.

The transfer device according to the invention, the installation and the method are herein not to be restricted to the application and implementation form described above. In particular, the transfer device according to the invention, the installation and the method may, for fulfilling a functionality herein described, comprise a number of respective elements, structural components and units that differs from a number herein mentioned.

BRIEF DESCRIPTION OF THE DRAWINGS

Further advantages will become apparent from the following description of the drawings. The drawings show an exemplary embodiment of the invention. The drawings, the description and the claims contain a plurality of features in combination. Someone skilled in the art will purposefully also consider the features individually and will find further expedient combinations.

It is shown in.

DESCRIPTION OF THE EXEMPLARY EMBODIMENT

Figure 1:
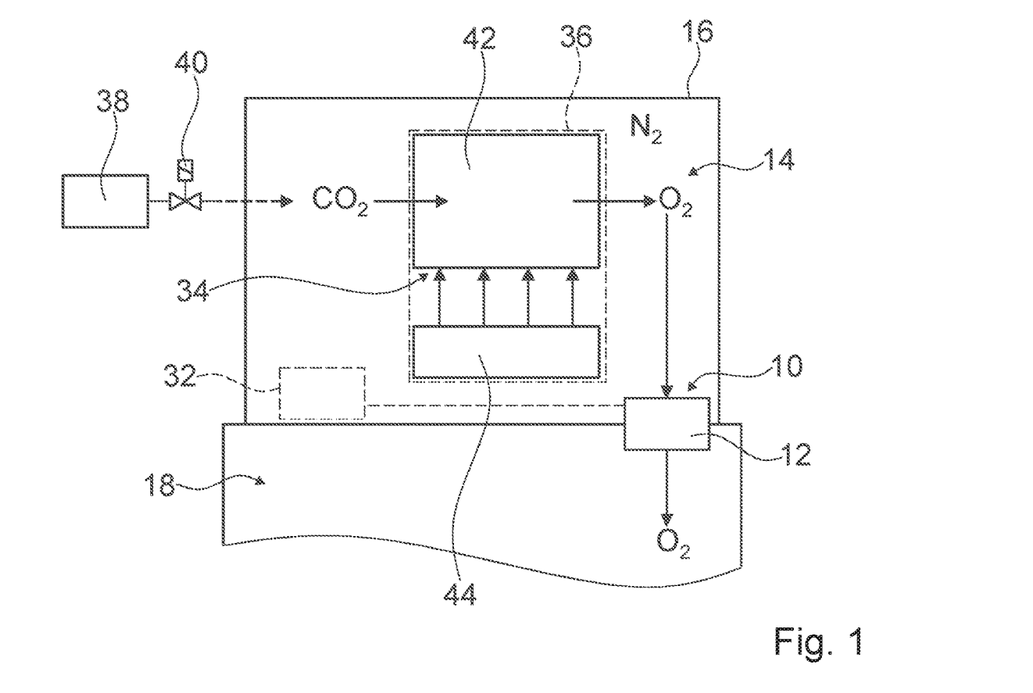
FIG. 1 an installation featuring a photobioreactor unit, a control and regulation unit and a transfer device in a schematic presentation, FIG. 2 the transfer device featuring a pump unit, which comprises a zirconium oxide element in a schematic presentation, FIG. 3 a partial section III-III of FIG. 2 of the transfer device in a schematic presentation, and FIG. 4 a diagram showing gas concentrations over time during exemplary operation of the installation with an algae reactor.

FIG. 1 shows an installation 16. The installation 16 is implemented by a photobioreactor installation. The installation 16 is provided for use in outer space. The installation 16 comprises a space 14. The space 14 is implemented by a closed-off space. Furthermore the installation 16 comprises a photobioreactor unit 36. Principally the installation 16 may also comprise a plurality of photobioreactor units 36. The installation 16 may principally also comprise other reactors which are deemed expedient by someone skilled in the art. The photobioreactor unit 36 is arranged in the space 14. The photobioreactor unit 36 is provided for receiving fed-in carbon dioxide $CO_2$ and for generating and outputting oxygen $O_2$ via photosynthesis, using a light source 44. The installation 16 comprises a gas tank 38. The gas tank 38 is implemented by a carbon dioxide tank. The gas tank 38 is connected to the space 14 by means of a valve via a line. The valve 40 is exemplarily implemented by a magnet valve. For a reaction of the photobioreactor unit 36, carbon dioxide $CO_2$ is conveyed into the space 14 from the gas tank 38. A quantity of carbon dioxide $CO_2$ is herein controlled via the valve 40.

The photobioreactor unit 36 is provided for production and/or cultivation of microorganisms, e.g. algae, cyanobacteria, moss plants, and/or phyto-cell cultures within an artificial technical environment. The photobioreactor unit 36 comprises an algae culture as an example of a photosynthetic system. The photobioreactor unit 36 is provided for using the photosynthesis process of produced and/or cultivated microorganisms for generating oxygen $O_2$ from light, carbon dioxide $CO_2$ and water via photosynthesis. The photobioreactor unit 36 comprises a receiving element 42 for receiving the microorganisms. The receiving element 42 may be implemented, for example, by a pipeline, a plate and/or another receiving element 42 deemed expedient by someone having ordinary skill in the art. The photobioreactor unit 36 further comprises a light source 44. The light source 44 is implemented by an artificial light source. Principally, however, it would also be conceivable that sunlight is used as a light source. The light source 44 is provided for an irradiation of the microorganisms during operation. The photobioreactor unit 36 forms a reaction area 34 of the installation 16.

The installation further comprises a transfer device 10. The transfer device 10 is implemented by a photobioreactor transfer device. The transfer device 10 is arranged between the first space 14 of the installation 16 and a second space 18. The second space 18 forms an environment of the installation 16. The second space 18 is embodied separate from the first space 14 of the installation 16. The second space 18 is in the present embodiment embodied by the cabin of a space station. The transfer device 10 borders both on the first space 14 and the second space 18. An operating pressure of the first space 14 may be between $10^{-3}$ mbar and 100 bar. An operating pressure of the second space 18 may be between the pressure of the first space 14 and 100 bar. Preferably an operation of the transfer device 10 is performed at ambient pressure, preferentially in a range of 750 mbar to 1250 mbar in the first space 14 and in a range of 800 mbar to 1500 mbar in the second space 18.

Furthermore the transfer device 10 comprises a pump unit 12. The pump unit 12 is provided for a defined gas transfer between the first, closed-off space 14 of the installation 16 and the second space 18, which is separate from the first space 14. The pump unit 12 is embodied as a selective oxygen pump. The pump unit 12 is implemented by an electro-chemical oxygen pump. The pump unit 12 further comprises a zirconium oxide element 20. The zirconium oxide element 20 is provided for a selective transfer of oxygen $O_2$ from the first space 14 into the second space 18.

Figure 2:
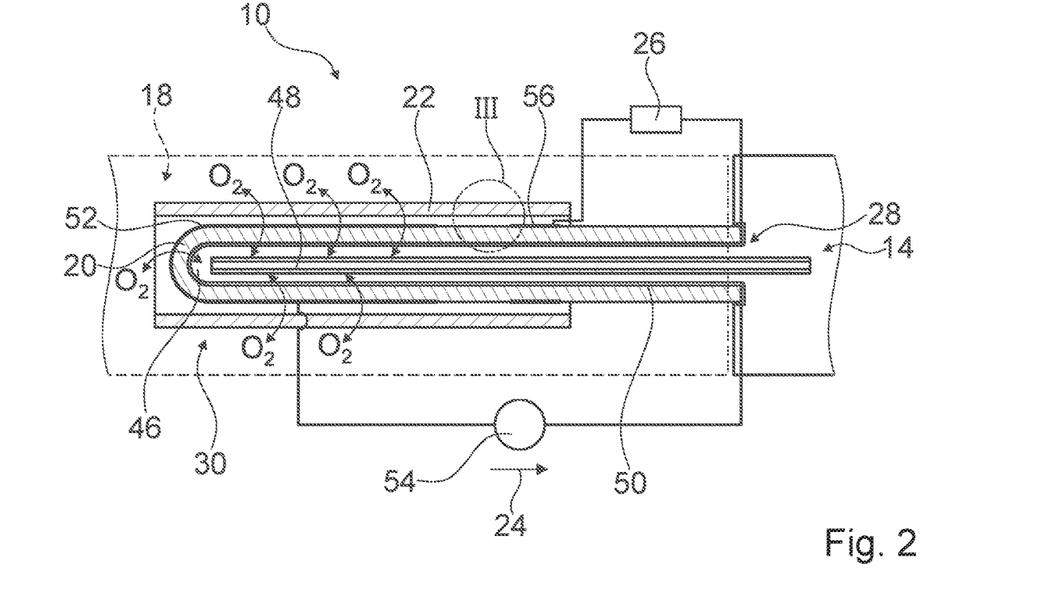

The zirconium oxide element 20 is embodied by a zirconium oxide ceramic. The zirconium oxide element 20 is implemented by a doped zirconium oxide element. The zirconium oxide element 20 is doped with yttrium oxide ($Y_2O_3$). Principally, it would however be also conceivable for the zirconium oxide element 20 to be embodied by a non-doped zirconium oxide element. For this purpose, the zirconium oxide element 20 is embodied by a zirconium oxide tube which is closed on one side. The zirconium oxide element 20 is embodied "test-tube-shaped". Principally, however, another shaping deemed expedient by someone skilled in the art is also conceivable. For example, a planar design of the zirconium oxide element 20 is also conceivable, the plane forming a separating plane between the two spaces 14, 18. The zirconium oxide element 20 hence forms a hollow space 46. The zirconium oxide element 20 protrudes into the second space 18 with a closed side. An open side of the zirconium oxide element 20 protrudes into the first space 14. Principally, however, it would also be conceivable that the zirconium oxide element 20 protrudes into the first space 14 with a closed side, an open side of the zirconium oxide element 20 protruding into the second space 18. The hollow space 46 of the zirconium oxide element 20 is connected to the first space 14. The pump unit 12 further comprises a guiding tube 48 protruding from the first space 14 into the hollow space 46. The guiding tube 48 serves for guiding gas flowing into the hollow space 46. The guiding tube 48 extends in parallel to the zirconium oxide element 20. The guiding tube 48 is paced apart from the zirconium oxide element 20. The guiding tube 48 extends up to shortly before a closed side of the zirconium oxide element 20. Via the guiding tube 48 gas can flow into the hollow space 46. Gas situated in the hollow space 46 is provided to flow in a gap of the hollow space 46, between the guiding tube 48 and the zirconium oxide element 20, out of the hollow space 46. As a result of this, advantageous circulation is achievable. Moreover, it is achievable that the hollow space 46 is flown through in an advantageously uniform fashion (FIG. 2).

Beyond this the pump unit 12 comprises two electrodes 50, 52. The electrodes 50, 52 are at least partly made of platinum. The electrodes 50, 52 are respectively implemented by a structured electrode having free spaces between the electrode material. The electrodes 50, 52 serve additionally as a catalyzer for a dissociation of oxygen-containing gases, e.g. $SO_2$, $CO_2$, $NO$, $NO_2$ or $O_3$, and/or for selectively separating off oxygen $O_2$. Principally, however, a different implementation of the electrodes which is deemed expedient by someone skilled in the art would be also conceivable. In particular, other electrode materials are conceivable, e.g. palladium, rhodium, cobalt, iridium and/or nickel. Principally, using a separate catalyzer, apart from the electrodes 50, 52 would also be conceivable. A first electrode 50 of the pump unit 12 is arranged on an inner side of the zirconium oxide element 20, which faces towards the hollow space 46. The first electrode 50 extends over a major part of an inner side of the zirconium oxide element 20. The first electrode 50 is arranged between the zirconium oxide element 20 and the first space 14. A second electrode 52 of the pump unit 12 is arranged on an outer side of the zirconium oxide element 20, which faces away from the hollow space 46. The second electrode 52 of the pump unit 12 is arranged on an outer side of the zirconium oxide element 20, on an end of the zirconium oxide element 20 which faces away from the open end of the zirconium oxide element 20. On a side of the zirconium oxide element 20 facing away from the open end of the zirconium oxide element 20, the zirconium oxide element 20 is encompassed by the second electrode 52 to a major part. The second electrode 52 is arranged between the zirconium oxide element 20 and the second space 18. The electrodes 50, 52 are connected to a power source 54 via lines. The power source 54 embodies a shared voltage source of the electrodes 50, 52. The power source 54 provides a pump flow. The zirconium oxide element 20 of the pump unit 12 is provided for bi-directional oxygen transfer between the first space 14 and the second space 18 (FIG. 2), depending on a polarity 24 of the pump flow.

The pump unit 12 also comprises a heating element 22. The heating element 22 is provided for heating the zirconium oxide element 20. The heating element 22 is provided for heating the zirconium oxide element 20 to an operating temperature and to keep it at said operating temperature. The heating element 22 is provided for heating the zirconium oxide element 20 to an operating temperature between 500° C. and 700° C. and to keep it at said operating temperature. The heating element 22 is implemented by an infrared radiant heater. Principally, however, a different implementation of the heating element 22 deemed expedient by someone skilled in the art would also be conceivable, in particular as a resistance heater. The heating element 22 is embodied tube-shaped. Principally, however, a different implementation deemed expedient by someone skilled in the art would also be conceivable. For example, in case of the zirconium oxide element 20 being embodied flat, in particular plate-shaped, the heating element 22 could principally also consist of two partial heating elements, which are respectively arranged on opposite sides of the zirconium oxide element 20. The heating element 22 encompasses the zirconium oxide element 20 on its outer surface in a region of the second electrode 52. The heating element 22 extends in parallel to a main extension direction of the zirconium oxide element 20. The heating element 22 is spaced apart from the zirconium oxide element 20 as well as from the second electrode 52 (FIG. 2).

Figure 3:
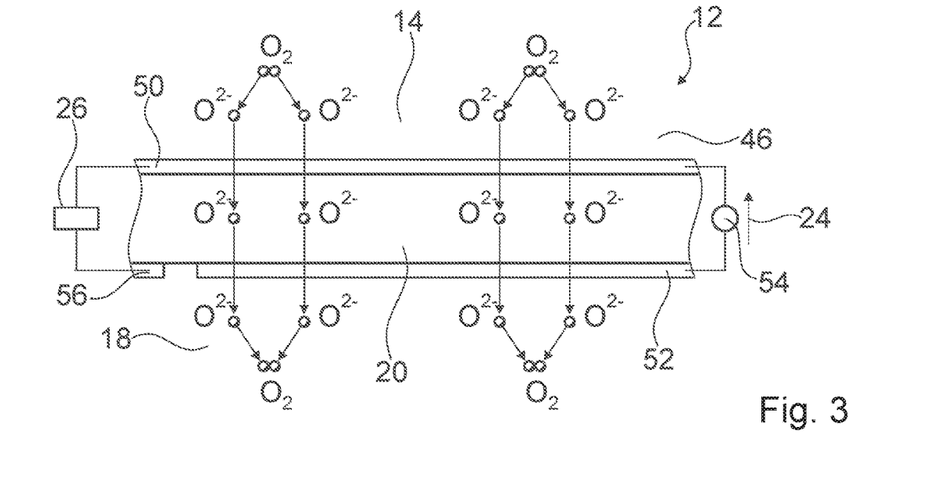

The zirconium oxide element 20 acts as a selective oxygen pump, transporting oxygen $O_2$ only if the zirconium oxide element 20 is at operating temperature and a pump flow is flowing between an inner side and an outer side of the zirconium oxide element 20. The pump unit 12 is herein provided for an electrical reduction of at least one gas. Under these operative conditions the zirconium oxide element 20 acts as an ion conductor and/or as a solid-matter electrolyte. The mode of operation of the pump unit 12 is that oxygen $O_2$ is selectively pumped out of a gas mixture in the first space 14 into the second space 18. The pump unit 12 is herein provided for specifically and selectively separating off oxygen $O_2$. Principally, however, the pump unit 12 may thus also be used for specifically accumulating a reduced gas in the first space 14 or the second space 18 (FIGS. 2 and 3).

The transfer device 10 further comprises a measuring unit 26. The measuring unit 26 is provided for capturing a voltage difference between two sides 28, 30 of the pump unit 12. The measuring unit 26 is provided for capturing a voltage difference between a first side 28, which faces towards the first space 14, and a second side 30 of the pump unit 12, which faces toward the second space 18. For this purpose the measuring unit 26 comprises a voltmeter. The measuring unit 26 is connected to the first electrode 50 of the pump unit 12 via a line. The measuring unit 26 is furthermore connected to a third electrode 56 via a line. The third electrode 56 is arranged on an outer side of the zirconium oxide element 20 that faces away from the hollow space 46. Principally, however, it would also be conceivable for the third electrode 56 to be arranged in another way that is deemed expedient by someone skilled in the art. The third electrode 56 is arranged on an outer side of the zirconium oxide element 20 between the open end of the zirconium oxide element 20 and the second electrode 52. The third electrode 56 is separate with respect to the second electrode 52 and has no electrical connection to the second electrode 52. The third electrode 56 is embodied annulus-shaped and extends around the zirconium oxide element 20. The third electrode 56 is arranged between the zirconium oxide element 20 and the second space 18. The measuring unit 26 is provided for capturing a voltage difference between the first electrode 50 and the third electrode 56. The measuring unit 26 is provided for deducting a pressure difference between the first space 14 and the second space 18 on the basis of the voltage difference. The measuring unit 26 is provided for deducting a partial pressure difference between the first space 14a and the second space 18 on the basis of the voltage difference. Beyond this a present oxygen concentration and/or differences in the oxygen concentrations of the spaces 14, 18 may be determined, in particular if an oxygen partial pressure in the first space 14 and/or in the second space are/is known (FIG. 2).

The installation 16 further comprises a control and regulation unit 32. The control and regulation unit 32 comprises a control electronics component. The control and regulation unit 32 is provided for regulating an absolute oxygen partial fraction in the first space 14 outside the reaction area 34 via the transfer device 10. The control and regulation unit 32 is provided for regulating an absolute oxygen partial fraction in the first space 14 outside a reaction area 34 to a value of approximately 15%. The control and regulation unit 32 is provided for monitoring the absolute oxygen partial fraction. The control and regulation unit 32 uses the measuring unit 26 of the transfer device 10 for monitoring the absolute oxygen partial fraction. Principally, however, it would also be conceivable that the control and regulation unit 32 comprises a separate sensor for monitoring the absolute oxygen partial fraction. The control and regulation unit 32 is provided for regulation an absolute oxygen partial fraction in the first space 14 outside a reaction area 34 by pumping off oxygen $O_2$ via the transfer device 10. For this purpose, the control and regulation unit 32 is provided to control the power source 54 of the pump unit 12. The pump rate of the transfer device 10 is influenced by the applied current rating. The pump rate of the transfer device is further influenced by a geometry, in particular a surface, of the zirconium oxide element 20. With a selected geometry, the current rating of the power source 54 is varied during operation to adjust the required oxygen transfer rate from the first space 14 into the second space 18 and to regulate the oxygen partial pressure in the first space 14 to a predetermined value. Principally the pump performance may also be adjusted via further electrical operation parameters, e.g. the operation temperature. The pump rate of the transfer device 10 can be varied in a range between a few milliliters per day and several liters per day, depending on dimensions of the zirconium oxide element 20 and on a strength of the pump flow.

Figure 4:
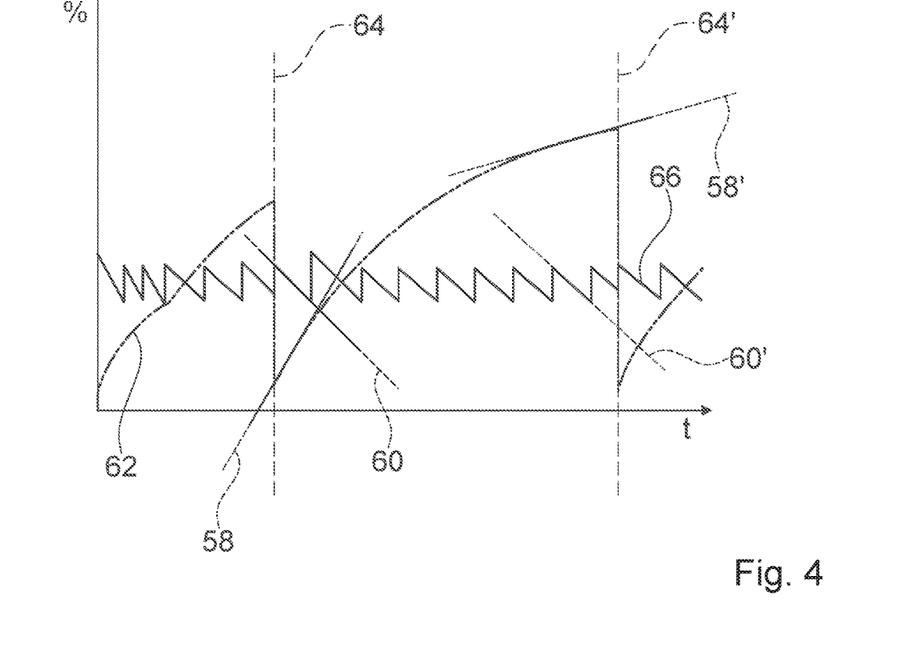

FIG. 4 shows an exemplary diagram of a measuring record of a gas concentration in the first space 14, in particular without a regulation as described above. The diagram shows an oxygen concentration 62 and a carbon dioxide concentration 66 in the space 14 over time t in %. Herein the diagram shows a variation of an oxygen output rate 58, 58' ($dO_2/dt$), respectively shown by tangents at points in time $t_1$ and $t_2$, out of the photobioreactor unit 36 depending on a constant carbon dioxide reception rate 60, 60' ($dCO_2/dt$), respectively shown by tangents at points in time $t_1$ and $t_2$, in the first space 14. In case of a constant carbon dioxide reception rate 60, the oxygen output rate 58 ($dO_2/dt$) decreases with increasing oxygen concentration 62 in the first space 14. Following a first exemplary rinsing process 64 of the first space 14 with nitrogen $N_2$ and addition of carbon dioxide $CO_2$, the molar oxygen output rate 58 is equal to the molar carbon dioxide reception rate 60 ($dCO_2/dt$). This behavior could be observed until an oxygen concentration 62 of approximately 15% in the first space 14. Above this the oxygen output rate 58 ($dO_2/dt$) decreases significantly. Hence a ratio of $dCO_2/dt=-dO_2/dt$ is achievable, which is equimolar as regards its absolute value, if the oxygen concentration 62 in the first space 14 outside the reaction area 14 is actively kept at a reduced value of approximately up to 15%. This results in a control variable of the oxygen concentration 62 of approximately 15%.

In a method for operating the installation 16 an absolute oxygen partial fraction in the first space 14 outside a reaction area 34 is regulated via the transfer device 10. The absolute oxygen partial fraction in the first space 14 outside a reaction area 34 is regulated via the transfer device 10 to a value of approximately 15%. For this purpose the control and regulation unit 32 controls the transfer device 10. For this purpose the control and regulation unit 32 controls the power source 54 of the pump unit 12 of the transfer device 10. Due to the voltage applied to the first electrode 50 and the second electrode 52, oxygen $O_2$ of the first space 14 is reduced to anions $O^{2-}$ by taking in electrons at the first electrode 50, which acts as a cathode. This reaction is supported by the platinum of the electrode 50 serving as a catalyzer. The anions $O^{2-}$ then migrate through the zirconium oxide element 20, which herein acts as an ion conductor and/or solid-matter electrolyte, to the second electrode 52. At the second electrode 52 the anions $O^{2-}$ react in the second space 18 back to oxygen $O_2$ by releasing the electrons (FIG. 3).

The method may principally also be performed in an ISRU application. The method is herein applicable for separating off and/or accumulating oxygen from a local gas mixture and/or from local solid bodies on the basis of In-Situ-Resource-Utilization (ISRU) applications on planets. Principally, the installation 16 may for this purpose also comprise alternative reactors. In particular, the installation 16 may comprise alternative reactors for physicochemical, biochemical and/or biological processes, which in particular release oxygen.

Furthermore, the method may principally also be performed in an Environmental Control System. The method may herein be used for pressure and temperature regulation as well as for oxygen supply in an at least substantially closed system, e.g. in particular a spacecraft, aircraft, landcraft or watercraft. Principally the installation 16 may for this purpose also comprise alternative reactors. In particular, the installation 16 may comprise alternative reactors for physicochemical, biochemical and/or biological processes.

The transfer device 10 is further used for monitoring and adjusting safety-relevant operating states. By means of the measuring unit 26 of the transfer device 10 a voltage difference between two sides 28, 30 of the pump unit 12 is captured. The measuring unit 26 captures, during operation of the installation 16, a voltage difference between a first side 28, which faces the first space 14, and a second side 30 of the pump unit 12, which faces the second space 18. Moreover the measuring unit 26 deducts, during operation of the installation 16, a partial pressure difference between the first space 14 and the second space 18 on the basis of the voltage difference (FIG. 3).

Performance of the method is effected under conditions of reduced or increased gravity. The method is performed in outer space, at local gravity values of $10^{-6}$ xg up to 10 xg. The method is applied in particular in outer space, e.g. at µg in a spaceship, in a process in a spaceship under accelerations of $10^{-6}$ xg up to 10 xg, on a planet, e.g. Mars, and/or on a natural satellite, e.g. the moon. However, the installation 16 and/or a reactor of the installation 16 may also be exposed to an artificial process acceleration which differs from the gravity values given. The gravity values may thus be increased drastically, e.g. for technical reasons, for example to 100 xg.

The invention claimed is:

1. An installation comprising
a first, closed-off space;
a transfer device with at least one pump unit for a defined gas transfer between the first space and a second space, which is separate from the first space and forms an environment of the installation, wherein the at least one pump unit is embodied as a selective oxygen pump, by which, independently of a prevailing gas mixture and as required, oxygen is selectively transferred out of the first space and into the second space or selectively transferred out of the second space and into the first space, which reduces or increases an oxygen concentration in the first space;
at least one photobioreactor unit for receiving fed-in carbon dioxide ($CO_2$), generating oxygen ($O_2$) via photosynthesis and outputting oxygen ($O_2$), wherein the photobioreactor unit is arranged in the first space, and
at least one control and regulation unit for regulating an absolute oxygen partial fraction in the first space, outside a reaction area of the at least one photobioreactor unit, to no more than 20% by controlling a power source of the pump unit, wherein the control and regulation unit comprises a control electronics component and a sensor for monitoring the absolute oxygen partial fraction.

2. The installation according to claim 1, wherein the at least one pump unit comprises at least one zirconium oxide element for a selective transfer of oxygen ($O_2$) out of the first space into the second space.

3. The installation according to claim 2, wherein the at least one pump unit comprises at least one heating element for heating the at least one zirconium oxide element.

4. The installation according to claim 2, wherein the at least one zirconium oxide element of the at least one pump unit is implemented by a doped zirconium oxide element.

5. The installation according to claim 2, wherein the at least one zirconium oxide element of the at least one pump unit bi-directionally transfers, depending on a polarity of a pump flow, oxygen between the first space and the second space.

6. The installation according to claim 1, wherein the at least one pump unit specifically and selectively separates oxygen ($O_2$).

7. The installation according to claim 1, wherein the at least one pump unit electrically reduces in at least one operating state at least one gas.

8. The installation according to claim 1, wherein the at least one pump unit accumulates a reduced gas in the first space and/or the second space.

9. The installation according to claim 1, wherein the transfer device comprises at least one measuring unit for capturing a voltage difference between at least two sides of the pump unit.

10. The installation according to claim 9, wherein the at least one measuring unit deducts a pressure difference between the first space and the second space on the basis of the voltage difference.

11. The installation according to claim 1, further comprising a control and/or regulation unit for controlling and/or regulating an absolute oxygen partial fraction in the first space outside a reaction area via the transfer device.

12. A method for operating the installation according to claim 1, wherein the method includes controlling, via the transfer device, an absolute oxygen partial fraction in the first space outside a reaction area.

13. The method according to claim 12, wherein the method includes using the transfer device for monitoring and/or for adjusting at least one safety-relevant operating state.

14. The installation according to claim 1, comprising a carbon dioxide tank, which is connected to the first space by a valve via a line, wherein for a reaction of the photobioreactor unit, carbon dioxide ($CO_2$) is conveyed into the first space from the carbon dioxide tank, wherein a quantity of carbon dioxide ($CO_2$) conveyed into the first space is controlled via the valve.

15. A transfer device with at least one pump unit for a defined gas transfer between a first, closed-off space of an installation and a second space, which is separate from the first space, wherein
the at least one pump unit is embodied as a selective oxygen pump and comprises at least one zirconium oxide element for a selective transfer of oxygen ($O_2$) out of the first space into the second space,
the zirconium oxide element is embodied as a tube, which is closed on one end and forms a hollow space inside,
the hollow space is connected to the first space but is closed-off from the second space, and the closed end of the zirconium element protrudes into the second space,
the at least one pump unit further comprises a guiding tube protruding from the first space into the hollow space,
the guiding tube is spaced apart from the zirconium oxide element and extends parallel to the zirconium oxide element to a point shortly before the closed end of the zirconium oxide element,
the guiding tube serves for guiding gas flowing into the hollow space, and
via the guiding tube, gas can flow into the hollow space, and gas situated in the hollow space flows in a gap of the hollow space, between the guiding tube and the zirconium oxide element, out of the hollow space to allow for circulation.

16. A transfer device according to claim 15, wherein the at least one pump unit further comprises two electrodes for catalyzing the dissociation of oxygen-containing gases, and wherein one electrode is positioned on an inner wall of the zirconium oxide element, which surrounds the hollow space, and the second electrode is positioned inside the second space on an outer wall of the zirconium oxide element.

17. A transfer device according to claim 15, wherein
the at least one pump unit further comprises at least one heating element for heating the zirconium oxide element,
the at least one heating element is positioned in the second space around the zirconium oxide element and the second electrode,
the at least one heating element extends parallel to a main extension direction of the zirconium oxide element, and the at least one heating element is spaced apart from the zirconium oxide element.

18. A transfer device according to claim 15, wherein the at least one zirconium oxide element is test-tube-shaped.

\* \* \* \* \*